US011706857B2

(12) United States Patent
Oelgarth et al.

(10) Patent No.: US 11,706,857 B2
(45) Date of Patent: Jul. 18, 2023

(54) SURGICAL LIGHT SYSTEM AND METHOD FOR OPERATING THE SURGICAL LIGHT SYSTEM

(71) Applicant: TRUMPF MEDIZIN SYSTEME GMBH + CO. KG, Saalfeld (DE)

(72) Inventors: Frank Oelgarth, Munich (DE); Denham Lansdell, Vaterstetten (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 209 days.

(21) Appl. No.: 17/214,019

(22) Filed: Mar. 26, 2021

(65) Prior Publication Data
US 2021/0307145 A1  Sep. 30, 2021

(30) Foreign Application Priority Data

Mar. 30, 2020  (EP) .................... 20166830

(51) Int. Cl.
F21Y 115/10 (2016.01)
F21W 131/205 (2006.01)
H05B 47/115 (2020.01)
A61B 90/35 (2016.01)
H05B 47/11 (2020.01)
H05B 47/155 (2020.01)

(52) U.S. Cl.
CPC ............ H05B 47/115 (2020.01); A61B 90/35 (2016.02); H05B 47/11 (2020.01); H05B 47/155 (2020.01); F21W 2131/205 (2013.01); F21Y 2115/10 (2016.08)

(58) Field of Classification Search
CPC .............. F21V 33/0068; F21V 21/403; F21W 2131/205; F21W 2131/202; F21W 2131/20
See application file for complete search history.

(56) References Cited

U.S. PATENT DOCUMENTS 7,311,410 B2 * 12/2007 Marka ................... F21V 21/403
362/418
9,310,096 B2 * 4/2016 Schreiber .............. F24F 13/078
10,099,368 B2  10/2018 Delspina
(Continued)

FOREIGN PATENT DOCUMENTS

CN  107388201 A  11/2017
EP  3056164 A1  8/2016
(Continued)

Primary Examiner — William J Carter
(74) Attorney, Agent, or Firm — Barnes & Thornburg LLP

(57) ABSTRACT

A surgical light system comprises several light sources configured to respectively generate a specific light field on at least one surgical site to generate a surgical light field, and a controller configured to control the several light sources such as to provide and adjust a brightness of the specific light fields. The surgical light field is divided into several adjacent sections, the several light sources are configured such that the sections are respectively covered by at least one of the specific light fields in order to have a resulting brightness, wherein the size of the at least one specific light field) correspond to the size of the covered section, and the controller is configured to control the light sources such that the resulting brightness of the sections is adjustable to a specific brightness.

14 Claims, 4 Drawing Sheets

(56) References Cited

U.S. PATENT DOCUMENTS

| | | |
|---|---|---|
| 10,240,751 B2 | 3/2019 | Zapata et al. |
| 2004/0008523 A1* | 1/2004 | Butler .................. A61N 5/0616 |
| | | 362/551 |
| 2008/0238338 A1 | 10/2008 | Latham et al. |
| 2008/0247163 A1* | 10/2008 | Chen ....................... F21V 14/06 |
| | | 362/311.06 |
| 2008/0273317 A1* | 11/2008 | Kaletin .................. A61B 90/36 |
| | | 362/33 |
| 2009/0122546 A1* | 5/2009 | Liu ........................... F21V 7/10 |
| | | 362/277 |
| 2009/0261759 A1 | 10/2009 | Fornasiero |
| 2009/0318772 A1 | 12/2009 | Marka et al. |
| 2010/0238282 A1 | 9/2010 | Cinqualbre et al. |
| 2010/0265703 A1* | 10/2010 | Hall ....................... H05B 33/02 |
| | | 362/231 |
| 2011/0015492 A1* | 1/2011 | Mangiardi ............ B65F 1/0093 |
| | | 600/249 |
| 2012/0014103 A1* | 1/2012 | Ye ........................... F21S 6/003 |
| | | 362/249.02 |
| 2012/0243666 A1* | 9/2012 | Lenchig, Jr. ......... A61B 6/4441 |
| | | 362/249.02 |
| 2013/0182417 A1* | 7/2013 | Amat Girbau .......... F21V 21/30 |
| | | 362/147 |
| 2013/0310652 A1 | 11/2013 | Barsoum et al. |
| 2015/0035440 A1 | 2/2015 | Spero |
| 2015/0369455 A1* | 12/2015 | Nieminen ............. F21V 21/104 |
| | | 362/428 |
| 2017/0105265 A1 | 4/2017 | Sadwick |
| 2017/0276324 A1 | 9/2017 | Zapata et al. |
| 2017/0367785 A1 | 12/2017 | Munari |
| 2019/0203920 A1 | 7/2019 | Strlin |
| 2020/0008282 A1 | 1/2020 | Pereyra et al. |

FOREIGN PATENT DOCUMENTS

| | | |
|---|---|---|
| EP | 3534769 A1 | 9/2019 |
| EP | 3374693 B1 | 10/2019 |
| EP | 2136129 B2 | 12/2019 |
| FR | 2913749 A1 | 9/2008 |
| WO | 0216824 A1 | 2/2002 |
| WO | 2015100384 A1 | 7/2015 |
| WO | 2018085058 A1 | 5/2018 |

* cited by examiner

SURGICAL LIGHT SYSTEM AND METHOD FOR OPERATING THE SURGICAL LIGHT SYSTEM

CROSS-REFERENCE TO RELATED APPLICATIONS

This application claims the benefit of European Patent Application Serial No. EP20166830.8, filed Mar. 30, 2020, the entire disclosure of which is incorporated herein by reference in its entirety.

BACKGROUND

The present disclosure relates to a surgical light system and a method for operating the surgical light system, in particular, to a surgical light system and a method for operating the surgical light system using LEDs as light sources.

More and more surgeries are being done in a minimal invasive set-up. Minimal invasive surgeries need specific, "to the point", lighting and would in addition profit from free "airspace" above a surgical field if less suspension arms holding equipment, e.g., for surgical lights, would be present. This would allow better visibility of, e.g., status monitors by the surgical team, improving work ergonomics and most likely reducing the probability of errors.

However, a common surgical theater will still have to be equipped with "traditional" surgical lights providing up to 160,000 lx for optimal surgical site illumination as there is always the risk that a minimal invasive surgery needs to become an open surgery in case of an emergency.

Therefore, the object underlying the present disclosure is to provide a surgical light system which may be placed outside the airspace above the surgical field and, nevertheless, provides a sufficient specific lighting without the need of directly operating functions of the surgical light system on light heads.

SUMMARY

The present disclosure includes one or more of the features recited in the appended claims and/or the following features which, alone or in any combination, may comprise patentable subject matter.

According to a first aspect of the present disclosure, a surgical light system comprises several light sources configured to respectively generate a specific light field on at least one surgical site to generate a surgical light field, and a controller configured to control the several light sources such as to provide and adjust the brightness of the specific light fields. The surgical light field is divided into several adjacent sections, wherein the several light sources are configured such that the sections are respectively covered by at least one of the specific light fields in order to have a resulting brightness. The size of the at least one specific light field corresponds to the size of the covered section, and the controller is configured to control the light sources such that the resulting brightness of the several sections is adjustable to a specific brightness.

By adjusting the brightness of the specific light fields which respectively cover the several respective sections into which the surgical light field is divided, the surgical site may be illuminated in an optimum manner. Sections requiring an increased resulting brightness may be easily illuminated by light sources which are controlled in a manner such that an emission of light is increased and sections in which the increased resulting brightness would disturb may be illuminated by light sources which are controlled in a manner such that the emission of light is reduced, e.g., by dimming the light sources. The resulting brightness of the individual sections of the several sections may therefore be adjusted respectively to a desired amount.

In an embodiment of the surgical light system, the resulting brightness of the several sections is adjustable within a range between the resulting brightness of the several sections when being unlit by the light sources and the brightness when being illuminated by the several light sources upon maximum performance. Having the option to switch off the several light sources to an unlit state in order to reduce the resulting brightness of the respective section and to operate the several light sources upon maximum performance enables a wide range of a resulting brightness of the several sections.

In a further embodiment of the surgical light system, the surgical light system comprises multiple LEDs and an optical device configured to generate the specific light fields. Due to the use of LEDS as light sources with little dimensions, a quantity of the light sources placed on a specific area may be increased so that the dimensions of a casing of the several light sources may be reduced or a large quantity of light sources may be accommodated in a casing. Following the reduced dimensions of the light sources, the optical device provided with an appropriate size according to the dimensions of the LEDs may be possible. Thereby, the optical device can comprise a facet lens.

In a further embodiment of the surgical light system, it is configured to generate the specific light fields on several surgical sites. By this characteristic, several surgical sites during one surgical intervention may be illuminated. Thereby, e.g., two surgical sites of one patient during a skin transplantation may be illuminated.

In a further embodiment of the surgical light system, the several light sources are configured to be integrated in a ceiling. By the light sources integrated in the ceiling, in particular, of the operating theater, the airspace above a surgical field may be kept free in order to enhance a visibility of, e.g., status monitors by the surgical team, to improve work ergonomics and most likely to reduce the probability of errors.

In another embodiment of the surgical light system, the surgical light system comprises a casing configured to be attachable to a ceiling of an operating theater and a mounting structure, and the several light sources are accommodated in the casing. By this implementation, a retrofitting is possible more easily and, in case of difficult spatial circumstances in the ceiling, attaching of the surgical light system may be possibly more simply.

In a further embodiment of the surgical light system, the casing may be configured to be immovably attachable to the ceiling of the operating theatre. Due to the immovable fixation, the location and posture of the light sources may be exactly defined so that a change of the light fields may be possible in a defined manner.

In a yet further embodiment of the surgical light system, the surgical light system comprises at least one position sensor configured to detect a position and a motion of an object, and a signal of the position sensor may be configured to be comprised in the input to the controller. By the provision of the motion sensor, various inputs for various functions for operating the surgical light system, for example, commands by gestures or detection of obstacles, are possible.

In a yet further embodiment of the surgical light system, at least some of the several sections are covered by at least two specific light fields, the at least one position sensor may be configured to detect a position and a motion of an object being located between a specific one of the several light sources and the surgical site, and the surgical light system may be configured to decrease an intensity of the specific one of the several light sources, and to increase an intensity of remaining light sources, the specific light field of which cover a same of the several sections as the specific light field of the specific one of the several light sources, to the specific brightness. Due to this characteristic, avoiding or reducing of shadows may be possible. The light of the specific one of the several light sources generating shadow on the surgical site may be decreased or switched off so that shadowing is reduced or avoided. For compensating the reduced resulting brightness due to the reduction of the light of the light source generating the shadow, an intensity of the remaining light sources illuminating the same section as the one of the several light sources may be increased. Therefore, the section may be illuminated with the required specific brightness without shadowing.

In a further embodiment of the surgical light system, the position sensor may be further configured to detect an orientation of the object. The object may comprise a pointer configured to be attachable to a headdress of a surgeon, and the surgical light system may be configured to increase the resulting brightness of the one of the several sections to which the pointer is directed. In this implementation, a headlight mode may be realized without the provision of a real headlight. Therefore, there is no need for wiring of the real headlight and the use is more comfortable for the surgeon since his movements are not restricted by the wiring. On the other hand, the advantages of the headlight, such as a direct adaption of an illuminated field to the head movement, are possible.

In a further embodiment of the surgical light system, the surgical light system comprises a brightness sensor configured to detect a brightness in the at least one surgical site, the brightness sensor may be configured to detect a location of an object, the brightness of which exceeds a predefined threshold in the at least one surgical site, and the surgical light system may be configured to decrease the brightness of the one of the several sections in which the object, the brightness of which exceeds a predefined threshold is located. When an illumination of an object having a brightness exceeding a predefined threshold such that the object glares the operating personnel, the glare may be decreased or removed in order to enhance the working condition of the operating personnel. Thereby, the intensity of the light sources illuminating the section in which the glaring object is located may be reduced so as to avoid the glaring.

According to a second aspect of the present disclosure, a method includes the steps of receiving an input by the controller, and controlling the several light sources such that a resulting brightness of one of the several sections covered by the light specific fields generated by the several light sources may be adjusted according to the input of the controller.

In some embodiments, adjusting the resulting brightness of the sections into which the surgical light field is divided, the surgical site may be illuminated in an optimum manner. Sections requiring an increased resulting brightness may easily be illuminated by light sources which are controlled in a manner such that an emission of light may be increased and sections in which the increased resulting brightness would disturb may be illuminated by light sources which are controlled in a manner such that the emission of light may be reduced. The resulting brightness of the individual sections of the several sections can therefore be adjusted respectively to a desired amount.

In an embodiment of the method, the input comprises an input from a position sensor detecting a position and a motion of an object, the object comprises a surgical marker, and the light sources are controlled such that the resulting brightness of at least one of the several sections determined by the surgical marker may be increased. According to a definition of a correlation between the surgical marker and the surgical light system, the resulting brightness of the sections may be increased. Depending on the definition, e.g., the section including the surgical marker and sections around the section including the surgical marker up to a defined perimeter are illuminated to have the specific brightness. On the other hand, the sections in an area between several surgical markers may be defined as to be illuminated to the specific brightness. Therefore, in case of a motion of the patient due to, e.g., a lateral adjustment of an operating table, the illumination may be adjusted accordingly.

In a further embodiment of the method, the input comprises an input from a position sensor detecting a position, a motion, and/or a direction of an object, the object comprises a pointer attached to a headdress of a surgeon, and the several light sources are controlled such that the resulting brightness of the one of the several sections to which the pointer is directed may be increased. In this embodiment, the headlight mode may be realized without the provision of a real headlight. Therefore, there may be no need for wiring of the real headlight and the use is more comfortable for the surgeon since his movements are not restricted by the wiring. On the other hand, the advantages of the head light such as a direct adaption of an illuminated field to the head movement are possible.

In a further embodiment of the method, the input comprises an input from a combined brightness and position sensor detecting a location of an object, the brightness of which exceeds a predefined threshold in the surgical site, and the light sources are controlled such that the brightness of the one of the several sections where the object is located may be decreased. When the illumination of the object having a brightness exceeding a predefined threshold, wherein the object glares the operating personnel, may be decreased, the glare may be reduced or removed in order to enhance the working condition of the operating personnel. Thereby, the intensity of the light sources illuminating the section in which the glaring object is located may be reduced so as to avoid the glaring.

In a yet further implementation of the method, the input comprises control data controlling the light sources to form specific shapes, such as letters, symbols or icons, by the specific light fields. According to appropriate input control data, the surgical light system may be used for projecting letters, words, sentences, symbols or icons on a target face. Thereby, e.g., a status of the surgical lamp system, or warning signals based on patient data input into the controller of the surgical light system may be displayed.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
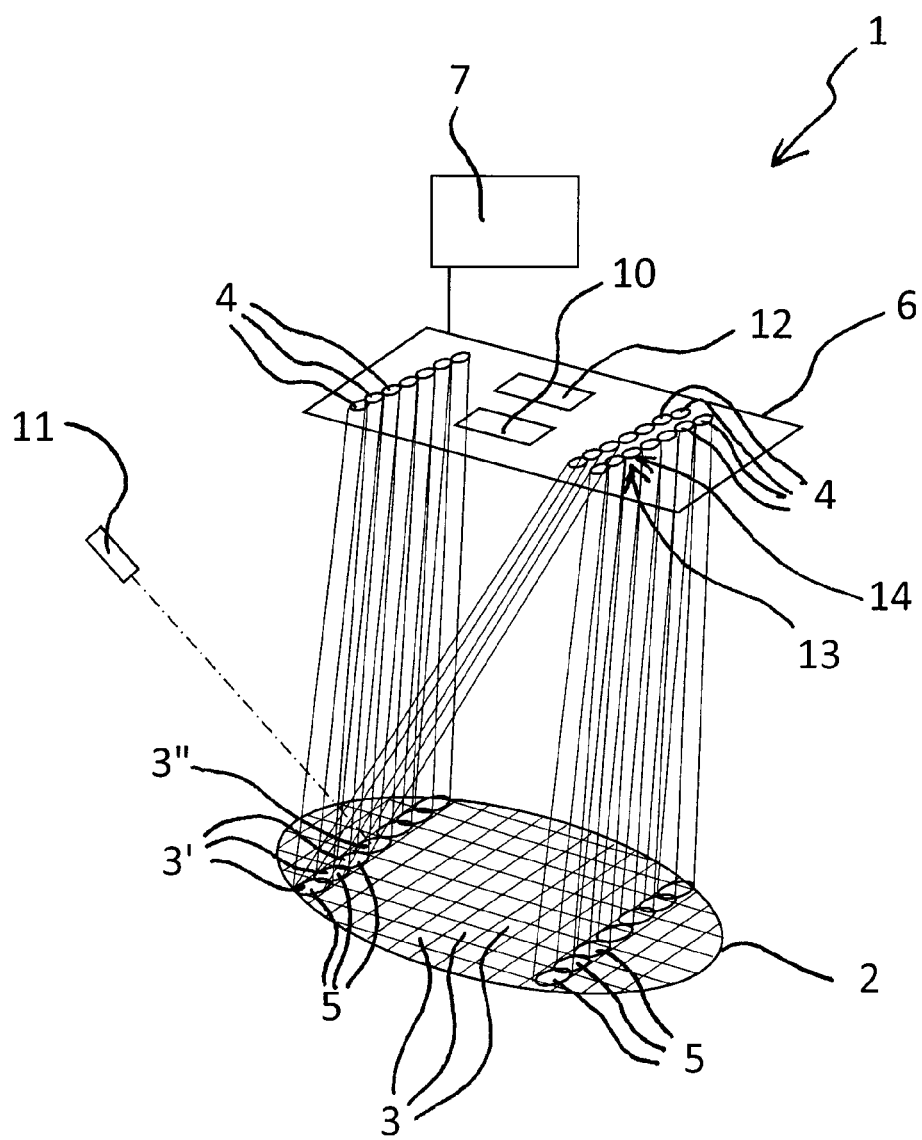
FIG. 1 shows a principle view of a surgical light system generating a surgical light field.

FIG. 1 shows a principle view of a surgical light system 1 generating a surgical light field 2. The surgical light field 2 is divided into several adjacent sections 3, 3', 3", wherein only some of the sections 3, 3', 3" are denominated with a reference sign. The surgical light field 2 is placed on a body of a patient, in particular, on a surgical site of the patient's body.

The surgical light system 1 comprises several light sources 4, wherein only some of the light sources 4 are denominated with a reference sign. The light sources 4 respectively generate a specific light field 5 on the surgical site. Thereby, the specific light fields 5 generate the surgical light field 2.

The light sources 4 are configured, particularly arranged, aligned, and generating a specific light field 5 having an appropriate size, such that the sections 3, 3', 3" are respectively covered by at least one of the specific light fields 5 in order to have a resulting brightness, wherein the size of the specific light field 5 corresponds to the size of the covered section 3, 3'. In this context, "the size of the specific light field 5 corresponds to the size of the covered section 3, 3', 3"" means that the size of the specific light field 5 is almost as large as the size of the section 3, 3'. 3", wherein the specific light field 5 can also cover a small portion of the adjacent section 3, 3', 3".

The surgical light system 1 comprises multiple LEDs 13 respectively equipped with an optical device 14 as the light sources 4 to generate the specific light fields 5. Several of the multiple LEDs 13 are equipped with a common optical device 14, such as a facet lens. In some embodiments, each of the LEDs 13 may have its own optical device or all of the LEDs 13 together have one optical device 14.

The colors of the LEDs 13 are selected such that an appropriate color temperature may be achieved. Optionally, the color temperature of the emitted light is adjusted. Further, also optionally, UV LEDs are provided in order to reduce germs in the surgical site.

The surgical light system 1 comprises a casing 6 accommodating all of the light sources 4. Alternatively, more than one casing 6 is provided or the surgical light system 1 does not comprise a specific casing 6 and the light sources 4 are arranged in another manner.

Further, the surgical light system 1 comprises a controller 7. The controller 7 controls the light sources 4 which means that the controller 7 controls specific electronics for dimming and turning on and off the light sources 4. Thereby, the controller 7 provides and adjusts a brightness of the specific light fields 5. To provide a brightness means that the light source 4 is switched on and no optical device obstructing a light beam of the light source 4 is provided or activated. Nevertheless, there are situations in which, during operation of the surgical light system 1, some of the light sources 4 are switched off or the light beam thereof is obstructed. By controlling the light sources 4, the resulting brightness of the sections 3, 3', 3" may be adjusted to a specific brightness.

As shown in FIG. 1, the sections 3, 3" are respectively covered by one specific light field 5 and the sections 3' are respectively covered by two specific light fields 5. Alternatively, all of the sections are covered by multiple specific light fields 5, a defined quantity of sections are covered by multiple specific light fields 5, or all of the sections are covered by one specific light field 5. In this last case, for providing a shadow-free illumination, several surgical light systems 1 are required.

The resulting brightness of the several sections 5 is adjustable within a range between the resulting brightness of the several sections 5 when being unlit by the light sources 4 and the resulting brightness of the several sections 5 when being illuminated by the light sources 4 upon maximum performance. The light sources 4 are dimmable. This means that the resulting brightness of the several sections 5 may be adjusted in a large range, namely, between unlit by the light source 4 or the light sources 4 and illuminated by the light sources 4 upon maximum performance. Thereby, the resulting brightness may be increased by turning on several light sources 4 generating a specific light field 5 covering the same section 3'. Since a risk of overheating and/or desiccation can occur, a temperature of this section 3' has to be monitored and, as the case may be, the brightness has to be reduced. Alternatively, all of the sections 3, 3', 3" are covered by the specific light fields 5 generated by light sources 4 which are all operated.

Figure 2:
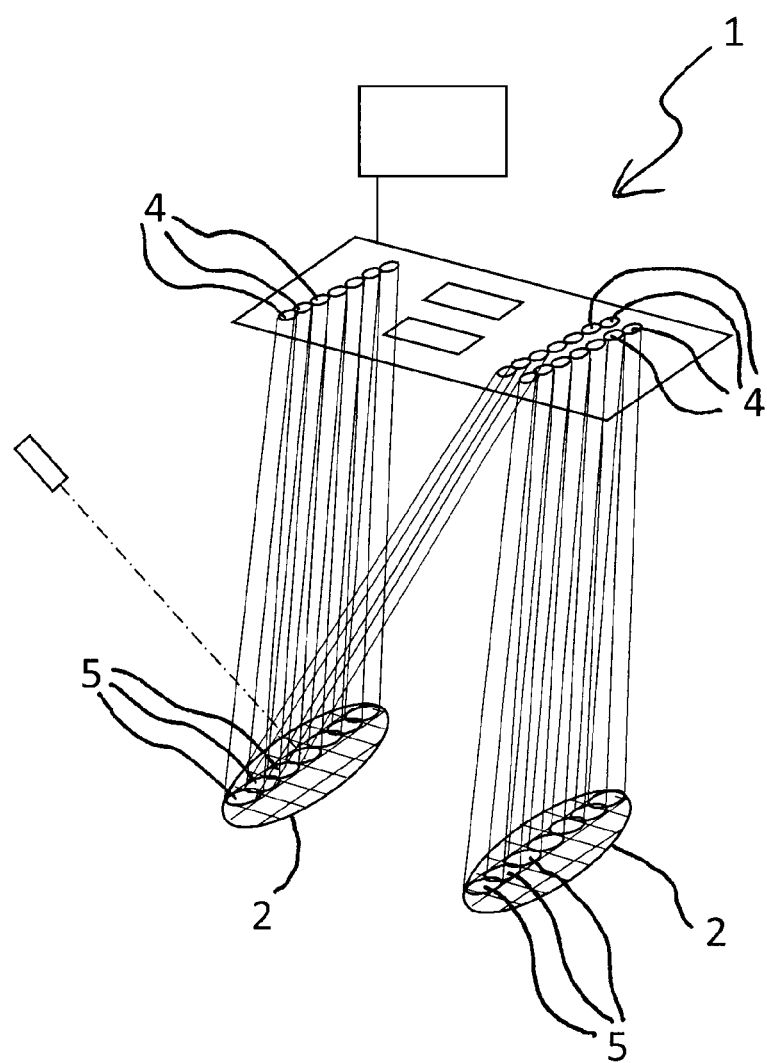
FIG. 2 shows an embodiment of the surgical light system generating two surgical light fields.

FIG. 2 shows an embodiment of the surgical light system 1 generating two surgical light fields 2. The surgical light system 1 generating two, or potentially more than two, surgical light fields 2 differs from the surgical light system 1 generating one surgical light field by a control routine of the surgical light system 1, wherein the light sources 4 generating the specific light fields 5 between the surgical light fields 2 are turned off.

Figure 3:
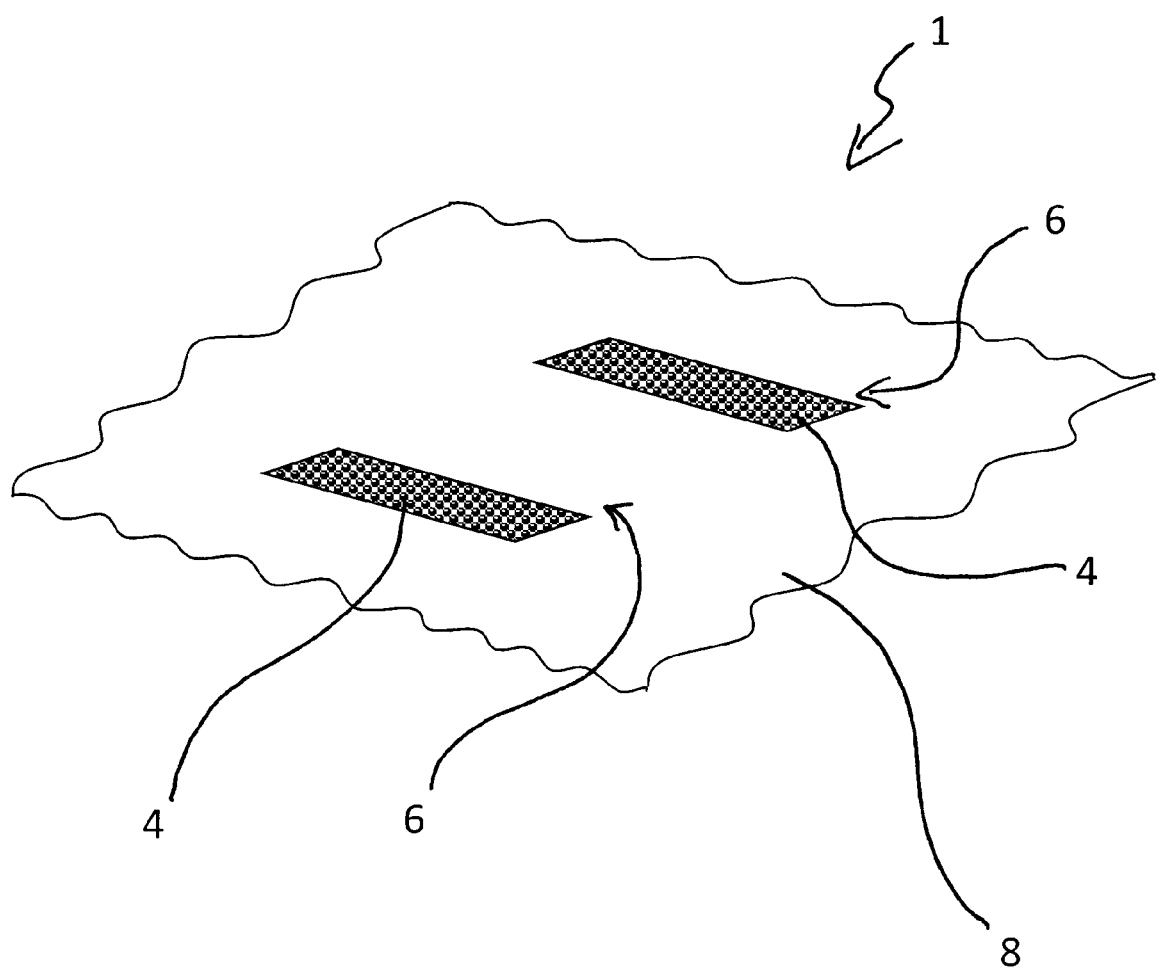
FIG. 3 shows the surgical light system integrated in a ceiling.

FIG. 3 shows the surgical light system 1 integrated in a ceiling 8. The light sources 4 of one surgical light system 1 are accommodated in two casings 6. The casings 6, and therefore, the surgical light system 1, are integrated in the ceiling 8, in particular, in a ceiling 8 of an operating theater. The light sources 4 are accommodated in the casings 6 in an immovable manner.

In some embodiments, the light sources 4 in the two casings 6 are assigned to different surgical light systems 1, the light sources 4 are accommodated in the casings 6 in a movable manner, or the light sources 4 are arranged in the ceiling 8 without casing.

Figure 4:
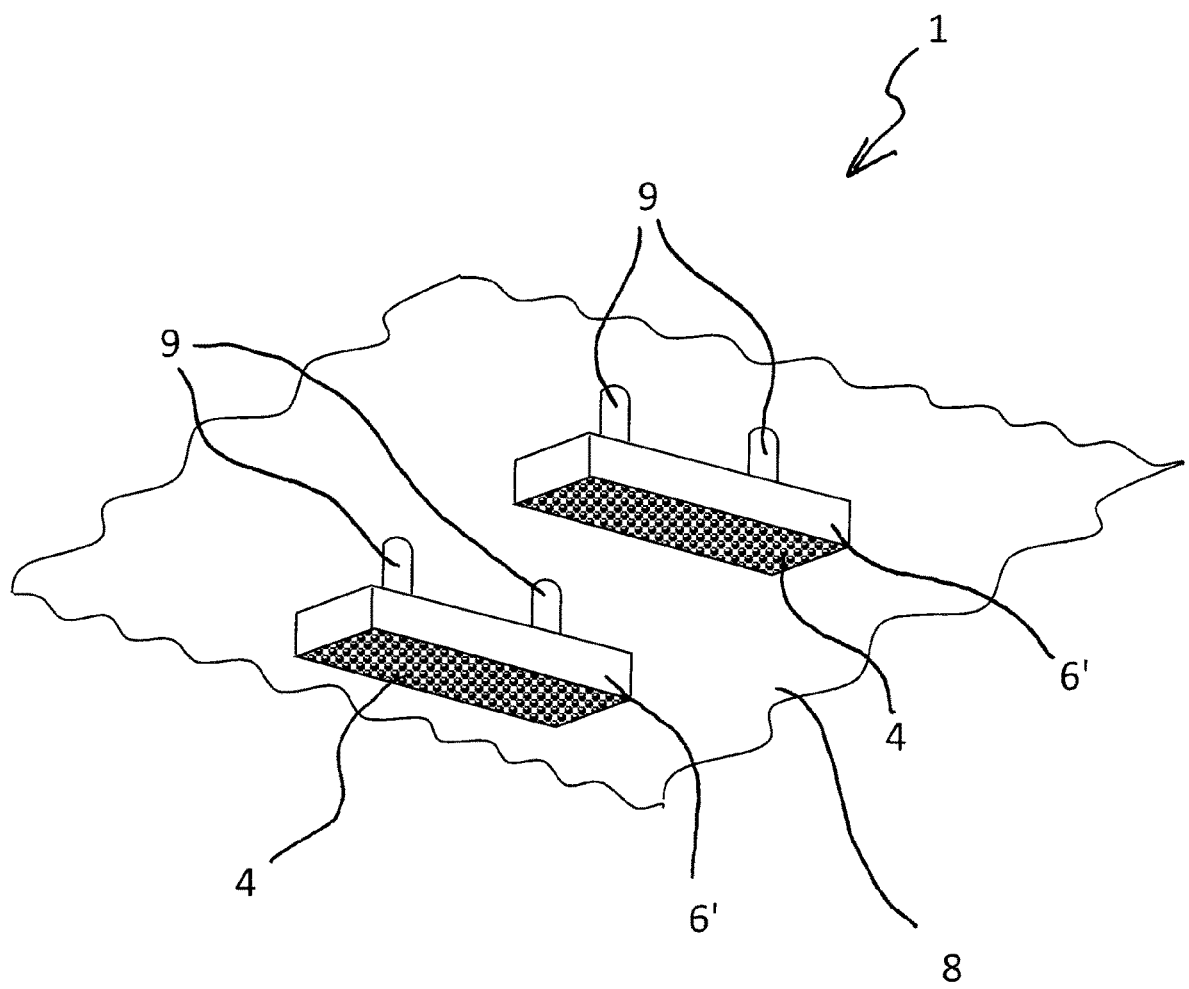
FIG. 4 shows the surgical light system comprising a casing and mounting structures.

FIG. 4 shows the surgical light system 1 comprising a casing 6' and mounting structures 9.

The surgical light system 1 shown in FIG. 4 differs from the surgical light system 1 of FIG. 3 in that the surgical light system 1 comprises the casings 6' attachable to the ceiling 8, particularly of an operating theater, and mounting structures 9.

The light sources 4 are immovably accommodated in the casings 6' and the casings 6' are immovably attached to the ceiling 8, particularly to the ceiling 8 of the operating theater which is much cost saving. Alternatively, the casings 6' are movably attached to the ceiling 8 and, in any case, the light sources are movably accommodated in the casing 6. In case of movability, motions of the light sources 4 and/or of the casings 6' are controlled by the controller 7. This enhances the performance of the surgical light system 1.

As also shown in FIG. 1, the surgical light system 1 comprises a position sensor 10. The position sensor 10 detects a position and a motion of an object, e.g., of a part of the body of a member of a surgical personnel, of a surgical instrument, etc. A signal of the position sensor is input to the controller 7.

As shown in FIG. 1, several of the sections 3' are covered by two specific light fields 5. The position sensor 10 is configured to detect a position and a motion of an object located between a specific one of the light sources 4 and the surgical site. The surgical light system 1 is configured to decrease an intensity of the specific one of the light sources 4 and to increase an intensity of remaining light sources 4, the specific light field 5 of which covers a same of the several sections 3' as the specific light field 5 of the specific one of the several light sources 4, to the specific brightness.

By this characteristic, shadow-management is possible. The intensity of the light source 4, the light beam of which is obstructed by the object, is decreased in order to avoid shadowing. On the other hand, the intensity of the remaining light sources 4, the specific light field 5 of which cover the same section 3' as the specific light field 5 of the specific one of the several light sources 4, is increased in order to achieve the specific brightness intended for the application.

Furthermore, the position sensor 10 is configured to detect an orientation of the object. In one embodiment, the object comprises a pointer 11. The pointer 11 is attached to a headdress of a surgeon. The surgical light system 1 increases the resulting brightness of the section 3" to which the pointer 11 is directed. By these features, a headlight mode of the surgical light system 1, wherein the brightness of the region eyed by the surgeon is increased, is possible.

In some embodiments, if the surgical light system 1 is not intended to have these functions, the surgical light system 1 may be provided without the position sensor 10.

Moreover, the surgical light system 1 comprises a combined brightness and position sensor 12 configured to detect a brightness in the surgical site. The combined brightness and position sensor 12 is configured to detect a location of an object, the brightness of which exceeds a predefined threshold, in the surgical site. Such an object may be an instrument having a reflective surface reflecting the light of the surgical light system 1. If the object, the brightness of which exceeds a predefined threshold, is detected in the surgical site, the resulting brightness of the sections 3, 3', 3" in which the object, the brightness of which exceeds a predefined threshold, is located is decreased. The combined brightness and position sensor comprises a camera. Alternatively, the combined brightness and position sensor comprises a light sensitive sensor.

In use, when the surgery is going to start, the surgical light system 1 is turned on. The surgical light system 1 uses defined pre-settings to pre-set a surgical site illumination. The pre-setting is chosen by a user interface or, alternatively, by an input-like recognition of specific people in a room. Alternatively, instead of using the defined pre-settings, a specific sequence of actions is performed to pre-set the surgical site illumination.

When the controller receives an input, this input may be received from a user interface, a distance measurement device, surgical site control sensors, or from a camera. The user interface can comprise a graphic user interface, a microphone, or sensors for gesture control. The distance measurement device can comprise a radar device, a laser device, a 3D IR device, or others. The surgical site control sensors can include a light intensity sensor, a temperature sensor, a spectroscopic sensor, or a photosensitive sensor.

Further alternatively or additionally, an automatic sequence may be performed. This sequence scans the surgical environment to recognize the position of an operating table or the position of a patient, a presence of a surgical robot, a presence of specific persons, such as surgeons, assistant surgeons, and their initial position relative to the operating table and the patient. A neuro, orthopedic or heart surgeon may be recognized by specific tags.

Alternatively or additionally, via a connection to an Electronical Medical Record (EMR) system, the surgical light system 1 receives information about the patient, such as weight or body height, and the surgery to be performed to adjust the initial setting in a better way. In the case of this connection, the participating surgeon and their specific preferences or subjects would be known to the surgical light system 1.

The several light sources 4 are controlled such that the resulting brightness of one of the several sections 3, 3', 3" covered by the light specific fields 5 generated by the several light sources 4 is adjusted according to the input to the controller 7.

In case that the input comprises an output from the position sensor 10 detecting the position and the motion of an object and the object is a surgical marker, the light sources 4 are controlled such that the resulting brightness of at least one of the several sections 3 determined by the marker is increased. In a specific case, a trocar may be used as the surgical marker. When the patient is moved, the surgical light system can adapt the sections to be illuminated or to be illuminated such as to be brighter.

When the surgeon uses the pointer 11 and the object detected by the position sensor comprises the pointer 11 attached to his headdress, the several light sources 4 are controlled such that the resulting brightness of the one of the several sections 3, 3', 3" to which the pointer 11 is directed is increased. Alternatively or additionally, further sections 3, 3', 3" adjacent to the section 3, 3', 3" to which the pointer 11 is directed are controlled such that their resulting brightness is increased.

If the input comprises an input from the combined brightness and position sensor 12 detecting a location of an object, the brightness of which exceeds a predefined threshold, in the surgical site, the light sources 4 are controlled such that the resulting brightness of the one of the several sections 3, 3', 3" where the object is located is decreased.

Furthermore, if desired, the input comprises control data controlling the light sources to form specific shapes, such as letters, symbols or icons, by the specific light fields. By using this feature, warning or information strings may be displayed on a specific face.

Moreover, in case of the surgical light system 1 integrated or attached to the ceiling 8, as the case may be, with small distance, the surgical light system 1 can supplement or replace a general operating room lighting. Optionally, such a light system 1 comprises multi-color LEDs and/or other light sources emitting light for direct or indirect ambient lighting.

While the present disclosure has been illustrated and described in detail in the drawing and the foregoing description, such illustration and description are to be considered illustrative or exemplary and not restrictive. The invention is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

Although this disclosure refers to specific embodiments, it will be understood by those skilled in the art that various changes in form and detail may be made without departing from the subject matter set forth in the accompanying claims.

The invention claimed is:

1. A surgical light system comprising
several light sources configured to respectively generate a specific light field on at least one surgical site to generate a surgical light field, and
a controller configured to control the several light sources such as to provide and adjust a brightness of the specific light fields, wherein
the surgical light field is divided into several adjacent sections,
the several light sources are configured such that the sections are respectively covered by at least one of the specific light fields in order to have a resulting brightness, wherein the size of the at least one specific light field corresponds to the size of the covered section, and
the controller is configured to control the light sources such that the resulting brightness of the sections is adjustable to a specific brightness, wherein the surgical light system comprises a combined brightness and position sensor configured to detect a brightness in the at least one surgical site, the combined brightness and position sensor is configured to detect a location of an object, the brightness of which exceeds a predefined threshold in the at least one surgical site, and the surgical light system is configured to decrease the resulting brightness of the one of the several sections in which the object, the brightness of which exceeds a predefined threshold, is located.

2. The surgical light system of claim 1, wherein the resulting brightness of the several sections is adjustable within a range between the resulting brightness of the several sections when being unlit by the light sources and the resulting brightness of the several sections when being illuminated by the several light sources upon maximum performance.

3. The surgical light system of claim 1, wherein the surgical light system comprises multiple LEDs and an optical device configured to generate the specific light fields.

4. The surgical light system of claim 1, wherein the surgical light system is configured to generate the specific light fields on several surgical sites.

5. The surgical light system of claim 1, wherein the several light sources are configured to be integrated in a ceiling.

6. The surgical light system of claim 1, wherein the surgical light system comprises a casing configured to be attachable to a ceiling of an operating theater and a mounting structure, and the several light sources are accommodated in the casing.

7. The surgical light system of claim 6, wherein the casing is configured to be immovably attachable to the ceiling of the operating theatre.

8. The surgical light system of claim 1, wherein the surgical light system comprises at least one position sensor configured to detect a position and a motion of an object, and a signal of the position sensor is configured to be comprised in the input to the controller.

9. The surgical light system of claim 8, wherein at least some of the several sections are covered by at least two specific light fields, the at least one position sensor is configured to detect a position and a motion of an object being located between a specific one of the several light sources and the surgical site, and the surgical light system is configured to decrease an intensity of the specific one of the several light sources, and to increase an intensity of remaining light sources, the specific light field of which cover a same of the several sections as the specific light field of the specific one of the several light sources, to the specific brightness.

10. The surgical light system of claim 8, wherein the position sensor is further configured to detect an orientation of the object, the object comprises a pointer configured to be attachable to a headdress of a surgeon, and the surgical light system is configured to increase the resulting brightness of the one of the several sections to which the pointer is directed.

11. A method for operating a surgical light including several light sources controlled by a controller, the light sources generating light fields sized to cover a respective section of a surgical site, the method including the steps of:
receiving an input by the controller; and
controlling the several light sources such that a brightness of one of the several sections covered by the light specific fields generated by the several light sources is adjusted according to the input to the controller, wherein the input comprises an input from a combined brightness and position sensor detecting a location of an object, the brightness of which exceeds a predefined threshold in the surgical site, and the light sources are controlled such that the resulting brightness of the one of the several sections where the object is located is decreased.

12. The method of claim 11, wherein the input comprises an input from a position sensor detecting a position and a motion of an object, the object comprises a surgical marker, and the light sources are controlled such that the resulting brightness of at least one of the several sections determined by the surgical marker is increased.

13. The method of claim 11, wherein the input comprises an input from a position sensor detecting a position, a motion, and/or a direction of an object, the object comprises a pointer attached to a headdress of a surgeon, and the several light sources are controlled such that the resulting brightness of the one of the several sections to which the pointer is directed is increased.

14. The method of claim 11, wherein the input comprises control data controlling the light sources to form specific shapes, such as letters, symbols or icons, by the specific light fields.

* * * * *